United States Patent [19]
Sakai et al.

[11] Patent Number: 5,965,413
[45] Date of Patent: Oct. 12, 1999

[54] PROCESS FOR PRODUCING PHOSPHATIDYLSERINES HAVING LONG CHAIN UNSATURATED FATTY ACID AS SIDE CHAIN

[75] Inventors: Masashi Sakai; Hideyuki Yamatoya; Satoshi Kudo, all of Tokyo, Japan

[73] Assignee: Kabushiki Kaisha Yakult Honsha, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/860,739

[22] PCT Filed: Nov. 6, 1996

[86] PCT No.: PCT/JP96/03237

§ 371 Date: Jul. 3, 1997

§ 102(e) Date: Jul. 3, 1997

[87] PCT Pub. No.: WO97/17460

PCT Pub. Date: May 15, 1997

[30] Foreign Application Priority Data

Nov. 8, 1995 [JP] Japan ................................ 7-313707

[51] Int. Cl.⁶ ................................ C12P 13/04; C12P 13/06; C12P 7/64; A61K 38/00
[52] U.S. Cl. ........................ 435/106; 435/116; 435/199; 558/169; 558/172
[58] Field of Search .................................... 435/106, 116, 435/199; 558/172, 169

[56] References Cited

U.S. PATENT DOCUMENTS

| | | | |
|---|---|---|---|
| 5,117,034 | 5/1992 | Ono et al. | 558/172 |
| 5,540,935 | 7/1996 | Miyazaki et al. | 424/450 |
| 5,700,668 | 12/1997 | DeFarra et al. | 435/106 |

FOREIGN PATENT DOCUMENTS

| | | |
|---|---|---|
| 63-245684 | 10/1988 | Japan . |
| 2-79990 | 3/1990 | Japan . |
| 5-336983 | 12/1993 | Japan . |
| 6-256179 | 9/1994 | Japan . |
| 6-279311 | 10/1994 | Japan . |

OTHER PUBLICATIONS

P.J. Delwaide et al, "Double–blind randomized controlled study of phosphatidylserine in senile demented patients", Acta Neurol Scand., vol. 73, 1986, pp. 136–140.

R.R. Engel et al, "Double–blind cross–over study of phosphatidylserine vs. placebo in patients with early dementia of the Alzheimer type", European Neuropsychopharmacology, vol. 2, 1992, pp. 149–155.

T. Cenacci et al, "Cognitive decline in the elderly: A double–blind, placebo–contolled multicenter study on efficacy of phosphatidylserine administration", Aging Clin. Exp. Res., vol. 5, No. 2, pp. 123–133, 1993.

B. F. Szuhaj & G.R. List, "Lecithins", American Oil Chemists' Society, U.S.A., 1985, pp. 145–149.

A. Bruni et al., "Pharmacological effects of phosphatidylserine liposomes", Nature, vol. 260, Mar. 1976, pp. 331–333.

A. Zanotti et al, "Chronic phosphatidylserine treatment improves spatial memory and passive avoidance in aged rats", Psychopharmacology Berl., vol. 99, 1989, pp. 316–321.

Primary Examiner—Herbert J. Lilling
Attorney, Agent, or Firm—Frishauf, Holtz, Goodman, Langer & Chick, P.C.

[57] ABSTRACT

A process for producing phosphatidylserine having a long chain unsaturated fatty acid in its side chain. In this process, a natural lecithin containing long chain unsaturated fatty acid side chain is used as the starting material. Using the natural lecithin as a substrate for reaction, phospholipase-D is caused to act on the substrate under the presence of serine, whereby phosphatidylserine having a side chain derived from the long chain unsaturated fatty acid can be easily obtained through a single step reaction.

15 Claims, No Drawings

PROCESS FOR PRODUCING PHOSPHATIDYLSERINES HAVING LONG CHAIN UNSATURATED FATTY ACID AS SIDE CHAIN

FIELD OF THE INVENTION

The present invention relates to a method for producing phosphatidylserines having a side chain derived from a long chain unsaturated fatty acid, more specifically, to a process for producing compounds effective for the prophylaxis and treatment of Parkinson's disease and dementia such as Alzheimer's disease, as well as effective for improving cerebration such as improved resistance against brain stress and improved learning effect.

BACKGROUND ART

A. Bruni, et al., report that the brain glucose level in mice injected via the caudal vein with phosphatidylserine extracted from bovine brain is increased by about 4 fold the level in the control group (A. Bruni et al., Nature, Vol. 260, pp. 331, 1976).

A. Zanotti et al., also report that the oral administration of phosphatidylserine extracted from bovine brain to aged rats with memory deficits for 12 weeks improved the performance of the aged rats (A. Zanotti et al., Psychopharmacology Berl., Vol. 99, pp. 316, 1989).

Furthermore it is confirmed at a double-blind placebo-controlled clinical trial for humans the efficacy of phosphatidylserine extracted from bovine brain in improving the memory impairment in Alzheimer's disease and during the aging stage (P. J. Delwaide et al., Acta Neurol. Scand., Vol. 73, pp. 136, 1986; R. R. Engel et al., Eur. Neuropsychopharmacol., Vol. 2, pp. 149, 1992; T. Cenacci et al., Aging Clin. Exp. Res., Vol. 5, pp. 123, 1993).

As has been described above, bovine brain-derived phosphatidylserine having the effect of increasing brain glucose level has an effect of improving the cerebration in rats and humans. Therefore, it is indicated that the degree of the increase in brain glucose level is an important indicator for selecting a substance with the action of improving cerebration.

However, it is believed that in general unsaturated fatty acid is bound to the beta position of phospholipid, and in natural phosphatidylserine, such as that derived from animal brain, more than ninety-two (92) percent of the fatty acid at beta position contains oleic acid (B. F. Szuhaj & G. R. List, "Lecithins", Am. Oil Chem. Soc., U.S.A., pp. 145, 1985).

In phosphatidylserines produced through a transphosphatidylation reaction with phospholipase-D (PLD), a known method of industrially producing phospholipids, most of fatty acid at beta position thereof was the same as that of the starting material, for example, linoleic acid and linolenic acid when using soybean lecithin, or oleic acid and linoleic acid when using yolk lecithin.

Recently, there have been conducted a variety of studies on n-3 and n-6 groups of long chain unsaturated fatty acids, and there have been conducted many laboratory animal experimentations on the physiologic activities of n-3 group long chain unsaturated fatty acids, including the improvement of learning performance. From these background, it may be possible that, if material combining above noted long chain unsaturated fatty acid and phosphatidylserine, such as phosphatidylserine comprising long chain unsaturated fatty acid in its molecule was produced, summation or synergistic effect of both phosphatidylserine and long chain unsaturated fatty acid will be effective and better cerebration improver may be obtained.

However, there is not known among currently available phosphatidylserine one which may be industrially produced with lower cost and comprises a long chain unsaturated fatty acid of n-3 or n-6 (except linoleic acid) group at beta position.

For example, it has been proposed that a phosphatidylserine derivative having a specific fatty acid at beta position of glycerol structure, which may activate proteinkinase-C (PKC) is a material which is a composition of long chain unsaturated fatty acid and phosphatidylserine for the estimation of the summation or synergistic effect as stated above (Japanese Patent-Laid Open No. 6-279311). In this Japanese patent, it is described that the experiment has been conducted in the condition that the phosphatidylserine derived from bovine brain which is effective for the clinical improvement of cerebration is a type of composition of a variety of fatty acids and the efficacy is not yet confirmed when structural fatty acid is specified, and also described that from the experiment conducted as such, specific proteinkinase-C activity has been confirmed if saturated fatty acid (14 to 18 carbon atoms) is at the alpha position and linoleic acid, linolenic acid, arachidonic acid, docosahexaenoic acid (DHA) are at the beta position.

For producing phosphatidylserine having such specific structure, a method is disclosed in the above identified Japanese patent that diacyl phospholipids are transformed to liso phospholipids with phospholipase $A_2$, then the specific phospholipid obtained by combining fatty acid in chemical synthesis arc transformed to phosphatidylserine through transphosphatidylation with phospholipase-D. This method is associated with complex multistage reaction and chemical synthesis so that the phosphatidylserine is not suitable for food stuff and that production cost is higher.

Also reported is that glycerol derivative having specific structure at alpha- and beta position fatty acids has the efficacy of improving learning performance (Japanese Patent Laid-Open No. 6-256179). However, this Japanese patent teaches that the primary structure for improvement is rather structural alpha- and beta fatty acids of the glycerol derivative, and the residue at gamma position, or glycerol-3-phosphoryl-X (X means hydroxyl, choline, or ethanolamine group) is not directly concerning to the improvement of the learning performance. Therefore, this glycerol derivative is different from the phosphatidylserine with summation or synergistic effect estimated as stated above in the combination of fatty acids having improvement effect of learning performance.

The producing method of glycerol derivative disclosed in the above noted second Japanese patent is of either separation from natural compound or of chemical synthesis or process with phospholipase-C, and this may not be a preferable method of industrial production for food.

DISCLOSURE OF THE INVENTION

The primary object of the present invention is to provide a method for producing phosphatidylserine having a long chain unsaturated fatty acid side chain in a relatively simple manner, thus necessitating fewer steps by overcoming above mentioned problems.

Another object of the present invention is to provide a method for readily producing phosphatidylserine of a type having as fatty acid structure n-3 or n-6 group long chain unsaturated fatty acid.

In accordance with an aspect of the present invention, there is thus provided a method for producing phosphatidylserine having a long chain unsaturated fatty acid side chain, and the method comprises preparing a substrate composed of a natural lecithin containing a long chain unsaturated fatty acid as a fatty acid side chain, and applying phospholipase-D to said natural lecithin of said substrate in the presence of serine to cause transphospharidylation reaction.

In accordance with a preferred embodiment of the present invention, said natural lecithin used for said substrate contains at least one type of the long chain unsaturated fatty acid selected from a group consisting of n-3 alpha linolenic acid, n-3 eicosapentaenoic acid, n-3 docosahexaenoic acid, n-6 linolenic acid, n-6 gamma-linolenic acid, and n-6 arachidonic acid.

In accordance with another embodiment of the present invention, said substrate is composed of a lecithin extracted from head tissue of sea fishes.

In accordance with still another embodiment of the present invention, said substrate is composed of a yolk lecithin extracted from eggs of hens fed with fish oil and/or vegetable oil containing a long chain unsaturated fatty acid.

In accordance with still another embodiment of the present invention, said substrate is composed of phosphatidylcholines fractionated and concentrated from the natural lecithin.

In accordance with yet another embodiment of the present invention, said substrate is composed of phosphatidylethanolamines fractionated and concentrated from the natural lecithin.

The principle of the present invention is based on a new findings that, if a natural lecithin having a long chain unsaturated fatty acid in the side chain at the beta position is used as a substrate for a transphosphatidylation reaction, phosphatidyl-L-serine having a long chain unsaturated fatty acid in its side chain at beta position can be obtained. According to this findings, phosphatidylserines having an abundance of the long chain unsaturated fatty acid may be easily produced through a single step transphosphatidylation reaction. Phosphatidylserines such produced may be an excellent cerebration improver which exhibits a variety of summation or synergistic effects of both phosphatidylserine and the long chain unsaturated fatty acid since it has an abundance of the long chain unsaturated fatty acid.

That is, according to the method of the present invention, a natural lecithin having a fatty acid side chain derived from a long chain unsaturated fatty acid is used as a substrate for a transphosphatidylation reaction, and phospholipase-D is caused to act on said natural lecithin under the presence of serine thereby obtaining phosphatidylserines having a fatty acid side chain derived from the long chain unsaturated fatty acid.

Natural lecithin especially suitable for use in the present invention contains at least one of long chain unsaturated fatty acid selected from the groups consisting of n-3 group such as alpha linolenic acid, eicosapentaenoic acid (EPA) and docosahexaenoic acid (DHA), and n-6 group such as linoleic acid, gamma-linolenic acid, and arachidonic acid. These long chain unsaturated fatty acids exhibit improving effect of learning performance, and a variety of physiological activities. Thus phosphatidylserines obtained from such natural lecithin containing these long chain unsaturated fatty acid may exhibit improving effect of learning performance and a variety of physiological activities.

Therefore, phosphatidylserine produced according to the present invention may be a cerebration improver exhibiting in a summation or synergistic manner the effect of cerebration improvement of the phosphatidylserine itself and above-mentioned other effects of the long chain unsaturated fatty acid contained in the molecules thereof.

In accordance with a method of the present invention, phosphatidylserine having a long chain unsaturated fatty acid in its side chain may be easily produced through only a single step of transphosphatidylation reaction by using natural lecithin containing a long chain unsaturated fatty acid as a substrate, without through a series of complex and multi step reactions or chemical synthesis processes of the conventional method. Therefore, in accordance with the present invention, cerebration improver which exhibits efficacy of both long chain unsaturated fatty acid and phosphatidylserine in a summation or synergistic fashion may be industrially advantageously produced with safety suitable for use in food applications as compared with the conventional method.

As the content of the long chain unsaturated fatty acid exhibiting physiologic activities as described above and contained in the phosphatidylserine in question is preferably as much as possible, natural lecithin used for the substrate in the present invention should preferably be selected such that it contains as much long chain unsaturated fatty acid as possible.

For the natural lecithin highly containing a long chain unsaturated fatty acid at the beta position, it is preferable to use a lecithin extracted from sea fishes which contains long chain unsaturated fatty acid in body tissue, especially in head tissue, such as for example, Tunas, Bonitoes, Mackerels, Sardines, Scombroids, Sauries, Horse Mackerels and Saurels, or yolk lecithin extracted from eggs of hens bred with feed stuff containing a long chain unsaturated fatty acid.

In practice, in order to obtain yolk lecithin highly containing long chain unsaturated fatty acid such as gamma linolenate, alpha linolenate, arachidonate, and docosahexaenate, a simple useful method for obtaining the yolk lecithin is to use eggs of hens fed with feed stuff supplemented with fish oil and/or vegetable oil containing such long chain unsaturated fatty acid. For example, soybean oil, perilla oil, cotton oil, sesame oil, corn oil, and safflower oil may be used as said vegetable oil. Thus the yolk lecithin having an abundance of the long chain unsaturated fatty acid can be extracted from the yolk of the eggs obtained from hens fed with feed stuff containing a long chain unsaturated fatty acid.

These natural lecithin contains primarily specific phospholipids, that is, phosphatidylcholine and phosphatidylethanolamine, and in addition in some cases phosphatidylglycerol. Thus, the natural lecithin may not be only used as substrate for reaction but also lecithin fractionated and concentrated to specific phospholipids such as phosphatidylcholine or phosphatidylethanolamine may be used as a substrate for the reaction of transphosphatidylation.

A desired lecithin is selected from the above-mentioned variety of natural lecithin and the concentrated extract thereof, and reacted with phospholipase-D in the presence of serine to conduct the transphosphatidylation using said serine as a receptor thereof, so that phosphatidylserines having an abundance of a long chain unsaturated fatty acid of the desired type may be obtained.

THE BEST MODE FOR CARRYING OUT THE INVENTION

EXAMPLE 1

For the first example of the present invention, phosphatidyl-L-serine was produced by using DHA-containing yolk lecithin as a starting material. The yolk lecithin used herein was extracted from eggs of hens fed with feed stuff supplemented by fish oil and vegetable oil containing a long chain unsaturated fatty acid, and is commercially available.

Initially, 1 g of yolk lecithin containing 10% DHA, 2 mL of ethyl acetate, 400 μL, of solution containing 120 mg of L-serine and 300 μL of enzyme solution of 150 U phospholipase-D (trade name: Phospholipase-D-Y1; manufactured by Yakult Honsha Co. Ltd., Japan) were prepared and sealed in a vial under nitrogen atmosphere and then stirred with shaking for incubation at 50° C. for 10 hours to conduct a transphosphatidylation reaction.

After the completion of the reaction, the vial was cooled, and paste precipitated at the bottom of the vial was dissolved with chloroform. The solution thus obtained was developed with thin layer chromatography (developer used contains chloroform-methanol-acetic acid at the volume ratio of 13:5:2) for separation. Dittomerlester reagent was sprayed onto the thin layer base to develop in color phosphorus to analyze phospholipid by using image analyzer (trade name: Geru-hakase; commercially available from Mitani Trading Co., Ltd, Japan). As a result of the analysis, development of 27.2% of phosphatidyl-L-serine was confirmed.

Also, the fixed phase of the spots of phosphatidyl-L-serine on the thin layer was scratched out and extracted with chloroform. Then, phospholipid fraction was separated from the extracts by means of capillary column chromatography. It was confirmed by the results from analysis that the phospholipid thus obtained contains 13% of DHA (22 carbon atoms, 6 double bonds).

As stated above, DHA containing yolk lecithin was used as reaction substrate for the transphosphatidylation reaction with phospholipase-D thereby producing phosphatidyl-L-serine which contains DHA.

The later Table 1 shows that the product contains 13% of DHA (C22:6), approximately 3% of linoleic acid (C18:2), and approximately 6% of arachidonic acid (C20:4).

EXAMPLE 2

For the second example of the present invention, phosphatidyl-L-serine was produced by using a lecithin obtained from the head muscle tissue of the Yellowfin tuna (*Thunnus Albacares*).

Initially, head of yellowfin tuna (approx. 1.6 kg) was crushed, pulverized, and freeze-dried to obtain dried-powder thereof. Then, for 100 g of the powder, solvent mixture of isopropanol, hexane and water (at the volume ratio of 10:20:3) was added to extract lipid fraction. The extract was concentrated and dried under vacuum. Dried lipid fraction (18 g) thus obtained was added to acetone and cooled with ice. The precipitation was dried to obtain approximately 300 mg of phospholipid.

Using this phospholipid, phosphatidyl-L-serine was produced. More specifically, 100 mg of phospholipid thus obtained by the above process, 2 mL of ethyl acetate, 400 μL of solution containing 120 mg of L-serine, and 300 μL of enzyme solution of 15 U phospholipase-D (trade name: phospholipase-D-Y1; manufactured by Yakult Honsha Co., Ltd., Japan) were prepared and sealed in a vial under a nitrogen atmosphere and then stirred with shaking for incubation at 50° C. for 10 hours to conduct a transphosphatidylation reaction.

After the completion of the reaction, the vial was cooled and a paste was precipitated at the bottom of the vial was analyzed by means of the thin layer chromatography and image analysis in a similar manner as that of Example 1 above. As a result of the analysis, it was confirmed that 34.5% of phosphatidyl-L-serine is developed in the phospholipid.

Further, in a similar manner as Example 1, the fixed phase of the spot of phosphatidyl-L-serine on the thin layer was scratched out and extracted with chloroform, and phospholipid fraction was separated from the extracts by means of capillary column chromatography. The analysis of the fatty acid showed that, as shown in the later Table 1, the phospholipid contains approximately 45% of DHA (C22:6) and 4% of EPA (C20:5).

As shown in this Example 2, a lecithin extracted from a head of Yellow fin Tuna was used as a substrate for the reaction, and phosphatidyl-L-serine which highly contains DHA was obtained by the transphosphatidylation reaction of the substrate with phospholipase-D.

EXAMPLE 3

For the third example of the present invention, phosphatidyl-L-serine was produced by using a starting material or lecithin obtained from the head muscle tissue of Bigeye Tuna (*Thunnus Obesus*).

Initially, approximately 1.2 kg of the head of Bigeye Tuna was crushed, pulverized and freeze-dried to obtain dry powder of Tuna head. Then, for 100 g of this powder, solvent mixture of sopropanol, hexane and water (at the volume ratio of 10:20:3) was added to extract lipid fraction. The extract was concentrated and dried under vacuum. Dried lipid fraction (10 g) thus obtained was added to acetone and cooled with ice. Then the precipitation thus developed was dried to obtain approximately 250 mg of phospholipid.

Using this phospholipid, phosphatidyl-L-serine was produced. More specifically, 100 mg of phospholipid thus obtained by the above process, 2 mL of ethyl acetate, 400 μL of solution suspending 120 mg of L-serine, and 300 μL of enzyme solusion containing 150 Uphospholipase-D (trade name: Phospholipase-D-Y1, manufactured by Yakult Honsha Co., Ltd., Japan) and 5 mg of $CaCl_2$ were prepared and sealed in a vial under a nitrogen atmosphere and then stirred with strong shaking for incubation at 50° C. for 10 hours to conduct transphosphatidylation reaction.

After the completion of reaction, the vial was cooled and a paste was precipitated at the bottom of the vial was analyzed by means of the thin layer chromatography and image analysis in a similar manner as that of Example 1 above. As a result of the analysis, it was confirmed that 82% of phosphatidyl-L-serine is developed in the phospholipid.

Further, in a similar manner as Example 1, the fixed phase of the spot of phosphatidyl-L-serine on the thin layer was scratched out and extracted with chloroform, and phospholipid fraction was separated from the extracts by means of capillary column chromatography. The analysis of the fatty acid showed that, as shown in the later Table 1, it has high content (approximately 88%) of EPA (C20:5) while content of DHA (C22:6) was 3%.

As shown in this Example 3, a lecithin extracted from the head of Bigeye Tuna was used as a substrate for the reaction, and phosphatidyl-L-serine especially highly containing EPA was obtained by the transphosphatidylation reaction with phospholipase-D.

EXAMPLE 4

For the fourth example of the present invention, phosphatidyl-L-serine was produced by using a starting material or lecithin obtained from the head muscle tissue of Ocean Bonito (*Katsuwonus pelamis*). Initially, approximately 0.5 kg of the head of Ocean Bonito was pulverized and freeze-dried to obtain dry powder thereof. Then, for 100 g of this powder, solvent mixture of isopropanol, hexane and water (at the volume ratio of 10:20:3) was added to extract lipid fraction. The extract was concentrated and dried under vacuum. Dried lipid fraction (11 g) thus obtained was added to acetone and cooled with ice. Then the precipitation was dried to obtain approximately 300 mg of phospholipid.

Using this phospholipid, phosphatidyl-L-serine was produced. More specifically, 100 mg of phospholipid thus obtained by the above process, 2 mL of ethyl acetate, 400 μL of solution containing 120 mg of L-serine, and 300 μL of enzyme solution of 15 U phospholipase-D (trade name: Phospholipase-D-Y1, manufactured by Yakult Honsha Co., Ltd., Japan) were prepared and sealed in a vial under a nitrogen atmosphere and then stirred with shaking for incubation at 50° C. for 10 hours to conduct a transphosphatidylation reaction.

After the completion of reaction, the vial was cooled and a paste was precipitated at the bottom of the vial was analyzed by means of the thin layer chromatography and image analysis in a similar manner as that of Example 1 above. As a result of the analysis, it was confirmed that 34% of phosphatidyl-L-serine is developed in the phospholipid.

Further, in a manner similar to Example 1, the fixed phase of the spot of phosphatidyl-L-serine on the thin layer was scratched out and extracted with chloroform, and phospholipid fraction was separated from the extracts by means of capillary column chromatography. The analysis of the fatty acid showed that, as shown in Table 1 below, the contents of DHA (C22:6) was approximately 45%, and EPA (C20:5) approx. 8%.

As shown in this Example 4, a lecithin extracted from the head of Ocean Bonito was used as a substrate for the reaction, and phosphatidyl-L-serine containing DHA and EPA was obtained by the transphosphatidylation reaction with phospholipase-D.

The following Table 1 shows the contents of each type of fatty acids (FA) in the phosphatidyl-L-serine obtained in the above examples 1 to 4.

Table 1

| FA type (C:double bond) | Contents of FA in phosphatidyl-L-serine (%) | | | |
|---|---|---|---|---|
| | Ex. 1 | Ex. 2 | Ex. 3 | Ex. 4 |
| C16:0 | 30 | 30 | 3 | 20 |
| C18:0 | 8 | — | — | — |
| C18:1 | 22 | 18 | 4 | 12 |
| C18:2 | 3 | — | — | — |
| C18:3 | 2 | — | — | — |
| C20:4 | 6 | — | — | — |
| C20:5 | — | 4 | 88 | 8 |
| C22:6 | 13 | 45 | 3 | 45 |

What is claimed is:

1. A process for producing phosphatidylserine having a long chain unsaturated fatty acid side chain, comprising preparing a substrate comprising natural lecithin containing a long chain unsaturated fatty acid as a tatty acid side chain, and applying phospholipase-D to said natural lecithin of said substrate in the presence of serine, said natural lecithin containing at least one long chain unsaturated fatty acid selected from the group consisting of n-3 eicosapentaenoic acid, n-3 docosahexaenoic acid and n-6 arachidonic acid.

2. The process according to claim 1, wherein said substrate is a lecithin extracted from head tissue of sea fish.

3. The process according to claim 1, wherein said substrate is a yolk lecithin extracted from eggs of hens fed with at least one oil selected from the group consisting of fish oil and vegetable oil containing at least one long chain unsaturated fatty acid selected from the group consisting of n-3 eicosapentaenoic acid, n-3 docosahexaenoic acid and n-6 arachidonic acid.

4. The process according to claim 1, wherein said substrate comprises phosphatidylcholines fractionated and concentrated from said natural lecithin.

5. The process according to claim 1, wherein said substrate comprising phosphatidylethanolamines fractionated and concentrated from said natural lecithin.

6. The process of claim 2, wherein the fish is selected from the group consisting of tuna, bonito, mackerel, sardine, scombroid and saurel.

7. The process of claim 3, wherein the vegetable oil is selected from the group consisting of soybean oil, perilla oil, sesame oil, corn oil and safflower oil.

8. The process of claim 1, wherein the natural lecithin is DHA-containing yolk lecithin.

9. The process of claim 8, wherein a transphosphatidylation reaction occurs at a temperature of 50° C. and for a reaction time of 10 hours.

10. The process of claim 1, wherein the natural lecithin is obtained from the head muscle of Yellowfin tuna.

11. The process of claim 10, wherein a transphosphatidylation reaction occurs at a temperature of 50° C. and for a reaction time of 10 hours.

12. The process of claim 1, wherein the natural lecithin is obtained from Bigeye tuna.

13. The process of claim 12, wherein a transphosphatidylation reaction occurs at a temperature of 50° C. and for a reaction time of 10 hours.

14. The process of claim 1, wherein the natural lecithin is obtained from ocean bonito.

15. The process of claim 14, wherein a transphosphatidylation reaction occurs at a temperature of 50° C. and for a reaction time of 10 hours.

\* \* \* \* \*